(12) United States Patent
Luo et al.

(10) Patent No.: US 7,261,877 B2
(45) Date of Patent: Aug. 28, 2007

(54) TRANSFER RESISTANT COSMETIC

(75) Inventors: Dexin Luo, Brooklyn, NY (US); Hernando Brieva, Manalapan, NJ (US); Milanka Susak, North York (CA); Tian Wang, Dix Hills, NY (US); Weilin Mu, Stony Brook, NY (US); Shahan Nazar, Garden City, NY (US); Wilson A. Lee, Hauppauge, NY (US)

(73) Assignee: E-L Management Corporation, Melville, NY (US)

( * ) Notice: Subject to any disclaimer, the term of this patent is extended or adjusted under 35 U.S.C. 154(b) by 631 days.

(21) Appl. No.: 10/623,968

(22) Filed: Jul. 21, 2003

(65) Prior Publication Data

US 2004/0141933 A1 Jul. 22, 2004

Related U.S. Application Data

(60) Provisional application No. 60/398,006, filed on Jul. 23, 2002.

(51) Int. Cl.
*A61K 8/00* (2006.01)

(52) U.S. Cl. .......................................................... 424/64
(58) Field of Classification Search .................. 424/64
See application file for complete search history.

(56) References Cited

U.S. PATENT DOCUMENTS

| 5,162,410 | A | 11/1992 | Sweet |
| 5,330,747 | A | 7/1994 | Krzysik |
| 5,451,610 | A | 9/1995 | Krzysik |
| 5,468,477 | A * | 11/1995 | Kumar et al. ............ 424/78.17 |
| 5,505,937 | A | 4/1996 | Castrogiovanni et al. |
| 5,512,272 | A | 4/1996 | Krzysik |
| 5,837,223 | A | 11/1998 | Barone et al. |
| 5,911,974 | A | 6/1999 | Brieva et al. |
| 5,965,112 | A | 10/1999 | Brieva et al. |
| 5,985,298 | A | 11/1999 | Brieva et al. |
| 6,071,503 | A | 6/2000 | Drechsler et al. |
| 6,074,654 | A | 6/2000 | Drechsler et al. |
| 6,139,823 | A | 10/2000 | Drechsler et al. |
| 6,274,152 | B1 | 8/2001 | Brieva et al. |
| 6,340,466 | B1 | 1/2002 | Drechsler et al. |
| 6,406,683 | B1 | 6/2002 | Drechsler et al. |
| 2002/0028223 | A1 | 3/2002 | Vatter et al. |
| 2003/0108498 | A1 * | 6/2003 | Stephens et al. .............. 424/63 |
| 2003/0198604 | A1 * | 10/2003 | Lawlor ........................ 424/49 |
| 2005/0008597 | A1 * | 1/2005 | Furukawa et al. ....... 424/70.12 |
| 2005/0276771 | A1 * | 12/2005 | Farsedakis et al. ........... 424/64 |
| 2006/0110346 | A1 * | 5/2006 | Lu ............................... 424/64 |

FOREIGN PATENT DOCUMENTS

| WO | WO 03/026596 A | 4/2003 |
| WO | WO 03/026599 A | 4/2003 |
| WO | WO 2004/073626 A | 9/2004 |

* cited by examiner

*Primary Examiner*—Sharon E. Kennedy
(74) *Attorney, Agent, or Firm*—Yongzhi Yang

(57) ABSTRACT

The invention relates to a topical composition for application to the lips comprising a reaction product of a silica dioxide, or a derivative thereof, with a dimethylsiloxy resin having a viscosity of about 1000 to about 200,000 cs, in combination with a volatile carrier.

25 Claims, No Drawings

TRANSFER RESISTANT COSMETIC

This application claims benefit of provisional application U.S. 60/398,006, filed Jul. 23, 2002.

FIELD OF THE INVENTION

The present invention relates to cosmetic compositions. More specifically, the invention relates to cosmetic compositions that are long-wearing and resistant to transfer onto clothing, utensils, and the like.

BACKGROUND OF THE INVENTION

When women are asked what cosmetic items they simply can't do without, lipstick routinely comes in as one of the top choices. Lipstick is clearly an essential cosmetic item to most women, and as technology improves, the demand for improved lip products grows. No longer is it adequate to have a large variety of shades to match any particular mood or outfit; women expect some value to be added to the product beyond the basic need of appealing color. Lip products now regularly incorporate biological actives and emollients that will actually improve the lip's condition, in addition to simply coloring it. Not only is treatment important to the lipstick purchaser, however; also crucial to the user is the lipstick's performance. Long gone are the days when a woman had the time or inclination to be touching up her makeup several times a day; it is now preferred that a cosmetic be put in place in the morning, and remain in place throughout the day, without any further attention. It is also now preferred that cosmetics, and particularly lipsticks, not leave their mark on unintended surfaces, such as coffee cups, napkins, utensils, a white blouse, or a kiss recipient's cheek. Thus, long wear and transfer resistance have become important characteristics to the consumer in choosing a new lipstick.

Fortunately, cosmetic technology has advanced to the point where it is possible to provide these desired traits in a lipstick. These types of products follow a general pattern: the use of a volatile solvent for quick drying, combined with a film-forming agent that lays down a long wearing film on the lips as the volatile solvent dries. For example, U.S. Pat. No. 5,505,937 discloses a transfer resistant lipstick which relies on the combination of a volatile solvent for quick drying, and a specified silicone ester wax to form a long-wearing film. U.S. Pat. Nos. 5,837,223; 5,911,974; 5,965,112; 6,274,152 and 5,985,298 disclose various cosmetics said to exhibit long wear, which cosmetics are based on a mixture of an "MQ"-type silicone resin, a volatile solvent and non-volatile oils. Similarly, U.S. Pat. Nos. 6,071,503; 6,074,654; 6,139,823; 6,340,466; 6,406,683 disclose long-wearing cosmetics that rely on the mixture of an "MQ"-type silicone resin and a high molecular weight dimethicone gum to achieve long wear and transfer resistance. Products based on these technologies are now also widely commercially available. Although such products have achieved to varying degrees a measure of success in providing long-wear and transfer resistance, one of the frequently noted problems with such products is the comfort the user experiences with their use. The chemical nature of the products is such that after several hours of wear, the products can leave the lips feeling very dry and flaky. To some extent, this is a reflection of a relative lack of flexibility in the film that remains on the lips after the volatiles flash off. Thus, although the film is responsible for the desirable characteristics, it is also responsible for some undesirable characteristics as well. Therefore, the search continues for a long-wearing, transfer resistant lipstick that provides the user with an improved level of comfort and flexibility, with a minimization of the characteristic dryness and flakiness that can be associated with use of the currently available products. The present invention provides such a product.

SUMMARY OF THE INVENTION

The present invention relates to cosmetic product for application to the lips, the product comprising (1) at least one silicone pressure sensitive adhesive that is the reaction product of silica dioxide, or derivatives thereof, with an organosiloxy resin having a viscosity of between about 1,000 to about 200,000 cs, preferably from about 10,000 to about 15,000 cs; and (2) a volatile carrier. The composition can be used alone to color the lips, or can be the base coat of a two part system, the second part comprising a top coat which contains at least one non-volatile solvent that is insoluble in both water and non-polar hydrocarbons, such as mineral oil. The resulting lip product is relatively non-drying, providing a comfortable, long-wearing film, and in combination with the top coat, provides a shiny, attractive lip color.

DETAILED DESCRIPTION OF THE INVENTION

The lip products of the present invention utilize as its film-forming component a pressure sensitive adhesive (PSA) compound that is a reaction product between a silica dioxide, or derivatives thereof, and a silanol-endblocked polydiorganosiloxane fluid having a viscosity of from about 1,000 to about 200,000 cs. Any silica derivative can be used, provided it has sufficient hydroxy radical density to react with the silanol-endblocked diorganosiloxane. In a preferred embodiment, the derivatives are tri(alkyl)organosilyl-end-blocked silica dioxide, reacted with a polydi(alkyl)organosiloxane having a viscosity of about 10,000 to about 15,000 cs. The preferred PSA compounds are non-flowable solids at room temperature, and have a viscosity well in excess of 10,000,000 cs. Examples of the manufacture of these materials are found in U.S. Pat. No. 5,162,410, the contents of which are incorporated herein by reference. U.S. Pat. Nos. 5,330,747 and 5,451,610, suggests their use in certain personal care products. However, to the best of Applicants' knowledge, these materials have not been previously suggested for use in a long-wearing, transfer resistant lip product. Preferred PSAs of the invention are available commercially from Dow Corning under the trade name BIO-PSA®. BIO-PSA® comes in two forms, standard and amine compatible, and are provided in a variety of solvents and resin-to-polymer ratios. Any of the BIO-PSA® materials is suitable for use in the present invention; however, preferred are the standard form adhesives, and particularly preferred is the BIO-PSA® identified by Dow Corning product number 7-4405, in an isododecane solvent.

To form the basic lip product, the PSA(s) is combined with one or more volatile carriers, to provide a rapid drying time on the lip. Any volatile oil that is a compatible carrier for the PSA can be used. Examples of useful oils for this purpose include both cyclic and linear silicones, such as octamethylcyclotetrasiloxane and decamethylcyclopentasiloxane(cyclomethicones); or straight or branched chain hydrocarbons having from 8-20 carbon atoms, such as decane, dodecane, tridecane, tetradecane, and C8-20 isoparaffins. Particularly preferred for this purpose are volatile dimethicones, cyclomethicones, and isododecane, either alone or in combination. To form the lip product base, the PSA, either in dry form, or in its commercially available fluid form, can be simply combined with the solvent and mixed to homogeneity at room temperature; however, mixing at higher temperatures, up to the boiling point of the materials, is also acceptable. The proportions of each component are not particularly critical; typically, the PSA is used in an amount of about 1 to about 50%, preferably about 5 to about 30% (solids content) by weight of the total composition, and the volatile solvent is present in an amount of about 5 to about 95% by weight, preferably about 20 to about 80%. The composition can also contain a plasticizer, a liquid silicone compatible ester, such as dioctyl malate, a fluid high molecular weight hydrocarbon, or a nonvolatile silicone having a viscosity ranging anywhere from 100 to 10,000,000 cs, in an amount of no more than about 20%, preferably about 1 to about 10% by weight.

Although the PSA-volatile solvent combination represent the components of the lip product base needed to achieve long wear and transfer resistance, it will ordinarily be desirable to provide additional components to add further functionality and/or aesthetics to the product. When the product is to be a lipstick, it will typically contain a certain amount of pigment. Any type of pigment, provided it is acceptable for use in the lip area, and with or without surface treatment, can be used in the product of the invention: examples of useful pigments include iron oxides (yellow, red, brown or black), titanium dioxide(white), zinc oxide, chrome oxide(green), chrome hydrate(green), ultramarines, manganese violet, ferric ferrocyanide, carmine 40, ferric ammonium ferrocyanide, or combinations thereof. Interference pigments, which are thin platelike layered particles having a high refractive index, which, at a certain thickness, produce interference colors, resulting from the interference of typically two, but occasionally more, light reflections, from different layers of the plate, can also be added to provide a pearlescence to the product, if such is desired.

Organic pigments may also optionally be included; these include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof. Stains, such as bromo dyes and fluorescein dyes can also be employed. Pigments when used are typically present in an amount of about 0.1 to about 30%, preferably about 0.1 to about 20%, by weight of the composition.

It is also possible to employ one or more cosmetic powders, for example, bismuth oxychloride, boron nitride, silica, polymethylmethacrylates, acrylates, kaolin, silk powder, nylon, barium sulfate, mica, sericite, muscovite, synthetic mica, titanium oxide coated mica, titanium oxide coated bismuth oxychloride, titanium oxide coated talc, platelet iron oxides, metal powders such as aluminum, lauroyl lysine, platelet talc and the like. If powders are used, the combined total of pigments plus powders will ordinarily be about 1 to about 30%, preferably, 0.1 to about 20%.

To enhance the aesthetics of the product, it is may be desired to incorporate a rheological modifier or oil-gelling material, i.e., an oil-soluble material that will modify the viscosity of the oil to the level desired in the final product. Examples of useful oil rheological modifiers or gellants include trihydroxystearin, dextrin fatty acid esters, such as dextrin palmitate; cholesterol and derivatives, such as lanosterol, silicone gellants, such as organopolysiloxane elastomers; oil soluble cellulose derivatives, such as ethyl cellulose, and polymers or mixed copolymers, such as ethylene/methacrylic acid copolymer, ethylene/acrylic acid copolymer, organo-clays, such as bentone, polyamides (amine-terminated, ester-terminated, acid-terminated, silicone-modified and tertiary amine terminated), N-acyl amino acids, and esters or amides thereof, 12-hydroxystearic acid and esters or amides thereof, alkylamides of di- and tricarboxylic acids, or polyethylene. The amount of the viscosity modifier, if used, is from about 0.5 to about 30%, preferably about 2 to about 10%, depending upon the nature of the gellants, and the desired end viscosity. These gellants in the indicated amounts will produce a flowable, soft gel product.

In an alternate embodiment, it may be desirable to confer structure on the composition. In such a case, the composition may contain wax or other structuring agents, so as to provide a self-supporting structure, e.g., a soft solid or stick product. Preferred structuring agents are waxes such as microcrystalline wax, beeswax, ozokerite, or ceresin, that are capable of structuring the volatile carrier. In some cases, the viscosity modifiers can also function as structuring agents, when used at higher levels or in higher molecular weight forms than in their use as viscosity modifiers. Examples of other structuring agents include, but are not limited to, polyamides, N-acyl amino acids or esters and amides thereof, polyethylene waxes, polybutene, or polyisobutene. These structuring agents may be used individually, or in combination. To form a solid, the structuring agent will generally be used in an amount of about 1 to about 50% by weight, preferably about 5 to about 30%, by weight of the composition.

The composition can also include other optional components that are traditionally included in lip products. For example, the composition may contain emollients, moisturizers, biologically active components, sunscreens or UV-absorbers, skin conditioners, such as skin lipids, emulsifiers, antioxidants, preservatives, and the like The composition will normally be anhydrous, but in certain embodiments may also contain some water. A preferred form of water-containing composition is a water-in-oil emulsion or dispersion. When an emulsion is prepared, there will preferably be present an appropriate emulsifier, for example, silicone copolyols, such as dimethicone copolyol or cetyl dimethicone copolyol, in order to enhance the stability of the composition.

The composition as described above can be used alone as a lipstick, lip gloss or lip balm. The film provided by such a composition is very flexible and non-drying, and therefore more comfortable, than previously available long wearing lip products. In most embodiments of the invention, the product will normally be liquid to pasty in texture, and therefore can be applied to the lips with a sponge, brush, or other implement appropriate to application of a product of this texture, although when in solid form it will be applied as usual with products of this type. In a preferred embodiment of the invention, the PSA-containing composition is used as a base coat for the lips, in combination with a separate top coat. The purpose of the top coat is to provide a glossy or shiny finish to the base coat, without disrupting the base coat's integrity. The top coat of the present invention must be sufficiently incompatible with the base coat, so as to not dissolve and thereby disturb the fastness of the base coat, and insoluble in water to prevent wear loss. To accomplish this, the top coat comprises as an essential element a primary component that is not soluble in either water or a non-polar hydrocarbon such as mineral oil. Such materials provide the right balance between incompatibility and adhesion with the base coat. Examples of such materials include, but are not limited to nonvolatile polar esters or oils, such as castor oil, or vegetable oils, poly(propylene glycol adipate), poly(2-methyl-1,3-propanediol adipate), or certain urethanes, such as octyldodecyl alcohol dimer/isophorone diisocyanate or isostearyl alcohol dimer/isophorone diisocyanate, or combinations thereof. The amount of "incompatible material" will depend upon the intended form of the final product. Like the base coat, the top coat can be either a flowable liquid or pasty product, or a soft solid or stick. Overall the amount of "incompatible material" can constitute from about 5 to about 99% of the top coat; for a flowable liquid or pasty product, the amount will preferably be about 50 to about 99%, and for a stick or solid, from 5 to about 50%, by weight of the top coat composition. As with the base coat, the top coat can comprise a viscosity modifier to produce a liquid or pasty product, or a structuring agent to form a soft solid or stick. The viscosity modifiers and structuring agents for the top coat can be selected from the same groups as for the base coat, depending upon the compatibility and gelling capabilities with regard to the chosen "incompatible material".

The top coat, like the base coat, will normally be anhydrous, but like the base coat, can also be an emulsion. Similarly, the top coat may contain the same types of optional components as the base coat, such as emollients, moisturizers, skin conditioners and the like, as well as gloss enhancing agents. The top coat may also contain pigments. The top coat is used in conjunction with the base coat as a two-part system. In normal application, the user applies the base coat to the lips, and allows the base coat to dry for a minute or two, thereby setting the durable film. When the base coat is dry the top coat is applied over the base coat, providing a shiny or glossy surface to enhance the appearance of the base coat. Each component can be provided as a separate item, for example, the top coat in a stick container and the base coat in a wand-type applicator suitable for pasty products, or each may be provided in separate pots or other applicators suitable for application of fluid products or stick products. In most cases, it will be preferred to provide the two components together in the same package, as part of a unified system or kit. In one such embodiment, each product can be provided as part of the same unit, i.e., a double-ended applicator containing separate reservoirs for each product. Possible variations of the proposed system will be readily apparent to one skilled in the art.

The invention is further illustrated by the following non-limiting examples.

EXAMPLE 1

This example provides formulations exemplifying the base coat of the present invention.

| Material | Weight % |
|---|---|
| A. | |
| Phase I | |
| Polyisobutene | 2.00 |
| Isododecane | 4.00 |
| *-continued* | |
| Material | Weight % |
| Phase II | |
| Dow Corning 7-4405 | 30.00 |
| isododecane/disteardimonium hectorite/propylene carbonate | 25.00 |
| stearyl dimethicone | 0.50 |
| isodocecane | 10.50 |
| Phase III | |
| Isododecane | 7.08 |
| Cetyl PEG/PPG-10/1 dimethicone/polyglyceryl-4 isostearate/Hexyl laurate | .12 |
| FD&C yellow No. 5 aluminum lake | 1.50 |
| Titanium dioxide | 2.40 |
| D&C red no. 7 calcium lake | 0.70 |
| Iron oxide | 0.10 |
| FD&C blue no 1 aluminum lake | 0.10 |
| Phase IV | |
| Mica | 15.00 |
| Mica/iron oxides/titanium dioxide | 1.00 |
| B. | |
| Phase I | |
| Trihydroxystearin | 2.67 |
| Isododecane | 13.33 |
| Phase II | |
| Dimethicone, 600,000 cs | 10.00 |
| Dow Corning 7-4405 | 30.00 |
| Phase III | |
| Isododecane/disteardimonium hectorite/propylene carbonate | 13.00 |
| Polytetrafluoroethylene | 0.90 |
| Mica | 4.00 |
| Phase IV | |
| Ceramide 3 | 0.05 |
| Cholesterol | 0.03 |
| Oleic acid | 0.02 |
| Phase V | |
| Isododecane | 8.10 |
| Cetyl PEG/PPG-10/1 dimethicone/polyglyceryl-4 isostearate/Hexyl laurate | 0.15 |
| Iron oxide yellow | 0.60 |
| Titanium dioxide | 4.00 |
| D&C red No. 7 calcium lake | 0.20 |
| Iron oxide black | 0.20 |
| FD&C blue No. 1 aluminum lake | 0.05 |
| Iron oxide red | 0.80 |
| Phase VI | |
| Mica | 8.00 |
| Dimethicone 200 cs | 3.90 |
| C. | |
| Phase I | |
| Trihydroxystearin | 2.30 |
| Isododecane | 11.50 |
| Dimethicone, 100,000 cs | 10.00 |
| Dow Corning 7-4405 | 30.00 |
| Nylon-6 | 0.75 |
| Mica | 3.50 |
| Vinyl dimethicone/methicone silsesquioxane crosspolymer | 1.50 |
| Olive oil | 1.00 |
| Isododecane/disteardimonium hectorite/propylene carbonate | 12.00 |
| Phase II | |
| Hectorite/hydroxyethylcellulose | 0.14 |
| Purified water | QS |
| Methyl paraben | 0.10 |
| Propyl paraben | 0.05 |
| Phase III | |
| Ceramide 3 | 0.05 |
| Cholesterol | 0.03 |
| Oleic acid | 0.02 |

-continued

| Material | Weight % |
| --- | --- |
| Phase IV | |
| Isododecane | 5.40 |
| Cetyl PEG/PPG-10/1 dimethicone/polyglyceryl-4 isostearate/ Hexyl laurate | 0.10 |
| Iron oxide yellow | 1.24 |
| Titanium dioxide | 1.00 |
| D&C red No. 7 calcium lake | 1.70 |
| Iron oxide black | 0.40 |
| FD&C blue No. 1 aluminum lake | 0.07 |
| Iron oxide red | 0.15 |
| Phase V | |
| Mica | 7.20 |
| Isododecane | 2.00 |
| Phase VI | |
| Dimethicone 200 cs | 3.00 |

EXAMPLE 2

This example provides formulations exemplifying the top coat of the present invention.

| Material | Weight % |
| --- | --- |
| A. | |
| Dibutyl lauroyl glutamide | 4.00 |
| Polyamide | 4.00 |
| Castor oil | 81.90 |
| PEG-7 olivate | 10.00 |
| BHT | .10 |
| B. | |
| Polyethylene (MW: 400-600) | 7.50 |
| Isostearyl alcohol dimer/isophorone diisocyanate | 24.90 |
| Octyl dodecanol dimer/isophorone diisocyanate | 40.00 |
| Hydrogenated coco-glycerides | 10.00 |
| Polyester | 15.00 |
| Organomodified silicone polyether copolymer | 0.40 |
| Stearoxymethicone/dimethicone polymer | 2.00 |
| Propyl paraben | 0.15 |
| BHT | 0.05 |

What is claimed is:

1. A two-part lip product comprising a base coat and a separate top coat, wherein the base coat comprises (a) a reaction product of a silica dioxide, or a derivative thereof, with an organosiloxy resin having a viscosity of about 1000 to about 200,000 cs, and (b) a volatile carrier, and wherein the top coat comprises at least one non-volatile solvent that is insoluble in both water and nonpolar hydrocarbons.

2. The two-part lip product of claim 1 in which (a) is a reaction product of a tri(alkyl)organosilyl-endblocked silica dioxide, reacted with a polydi(alkyl)organosiloxane having a viscosity of about 10,000 to about 15,000 cs.

3. The two-part lip product of claim 1 in which the volatile carrier is selected from the group consisting of cyclic or linear volatile silicones, straight or branched chain hydrocarbons having from 8 to 20 carbon atoms.

4. The two-part lip product of claim 1 which also comprises a rheological modifier.

5. The two-part lip product of claim 4 in which the rheological modifier is selected from the group consisting of trihydroxystearin; dextrin fatty acid esters; cholesterol and derivatives thereof silicone gellants; oil soluble cellulose derivatives; oil soluble or swellable polymers or copolymers; organo-clays; polyamides; N-acyl amino acids, and esters and amides thereof 12-hydroxystearic acid and esters and amides thereof; alkylamides of di- and tricarboxylic acids, and polyethylene; and mixtures thereof.

6. The two-part lip product of claim 1 which also comprises a structuring agent.

7. The two-part lip product of claim 1 which also comprises a plasticizer.

8. The two-part lip product of claim 1 which also comprises at least one pigment or cosmetic powder.

9. The two-part lip product of claim 1, wherein the top coat provides a glossy or shiny finish without disrupting the base coat's integrity.

10. The two-part lip product of claim 1, wherein the nonvolatile solvent is selected from the group consisting of nonvolatile polar esters or oils, caster oil, vegetable oils, poly(propylene glycol adipate), poly(2-methyl-1,3-propanediol adipate), urethanes, octyldodecyl alcohol dimer, isophorone diisocyanate or isostearyl alcohol dimer, isophorone diisocyanate, and combinations thereof.

11. The two-part lip product of claim 1, wherein the nonvolatile solvent is selected from the group consisting of nonvolatile polar esters or oils, caster oil, vegetable oils, poly(propylene glycol adipate), poly(2-methyl-1,3-propanediol adipate), urethanes, octyldodecyl alcohol dimer, isophorone diisocyanate or isostearyl alcohol dimer, isophorone diisocyanate, and combinations thereof.

12. A two-part lip product comprising a base coat and a separate top coat, wherein the base coat comprises (a) a reaction product of a tri(alkyl)organosilyl-endblocked silica dioxide, reacted with a polydi(alkyl)organosiloxane having a viscosity of about 10,000 to about 15,000 cs, and (b) a volatile carrier selected from the group consisting of cyclic or linear volatile silicones, straight or branched chain hydrocarbons having from 8 to 20 carbon atoms, and wherein the top coat comprises at least one non-volatile solvent that is insoluble in both water and nonpolar hydrocarbons.

13. The two-part lip product of claim 12, wherein the top coat provides a glossy or shiny finish without disrupting the base coat's integrity.

14. The two-part lip product of claim 12 in which the volatile carrier is a straight or branched chain hydrocarbon having from 8 to 20 carbon atoms.

15. The two-part lip product of claim 12 which comprises at least one rheological modifier selected from the group consisting of trihydroxystearin; dextrin fatty acid esters; cholesterol and derivatives thereof; silicone gellants; oil soluble cellulose derivatives; oil soluble or swellable polymers or copolymers; organo-clays; polyamides; N-acyl amino acids, and esters and amides thereof 12-hydroxystearic acid and esters and amides thereof alkylamides of di- and tricarboxylic acids, and polyethylene; and mixtures thereof.

16. The two-part lip product of claim 12 which also comprises a plasticizer selected from the group consisting of a liquid silicone-compatible ester, a fluid high molecular weight hydrocarbon, or a nonvolatile silicone having a viscosity between about 100 to about 10,000,000 cs.

17. A transfer-resistant topical system for application to the lips comprising (1) a base coat comprising (a) a reaction product of a silica dioxide, or a derivative thereof, with a organosiloxy resin having a viscosity of about 1000 to about 200,000 cs, and (b) a volatile carrier; and (2) a top coat comprising a primary component that is not soluble in either water or a nonpolar hydrocarbon.

18. The system of claim 17 in which the base coat (1) comprises (a) a reaction product of a tri(alkyl)organosilyl-endblocked silica dioxide with a polydi(alkyl)organosiloxane having a viscosity of about 10,000 to about 15,000 cs, and (b) a volatile carrier selected from the group consisting of cyclic or linear volatile silicones, straight or branched chain hydrocarbons having from 8 to 20 carbon atoms, and top coat (2) comprises a primary component selected from the group consisting of nonvolatile polar esters and oils; urethanes, and mixtures thereof.

19. The system of claim 18 in which the base coat also comprises a rheological modifier selected from the group consisting of trihydroxystearin; dextrin fatty acid esters; cholesterol and derivatives thereof; silicone gellants; oil soluble cellulose derivatives; oil soluble or swellable polymers or copolymers; organo-clays; polyamides; N-acyl amino acids, and esters and amides thereof; 12-hydroxystearic acid and esters and amides thereof; alkylamides of di- and tricarboxylic acids, and polyethylene; and mixtures thereof.

20. The system of claim 18 which also comprises at least one pigment or cosmetic powder.

21. The system of claim 18 which also comprises a plasticizer, selected from a group consisting of a liquid silicone-compatible ester, a fluid high molecular weight hydrocarbon, and a nonvolatile silicone having a viscosity between about 100 to about 10,000,000 cs.

22. The system of claim 18 which also comprises a structuring agent.

23. The system of claim 18 in which the base coat (1) comprises (a) a reaction product of a tri(alkyl)organosilyl-endblocked silica dioxide with a polydi(alkyl)organosiloxane having a viscosity of about 10,000 to about 15,000 cs; (b) a volatile carrier selected from the group consisting of cyclic or linear volatile silicones, straight or branched chain hydrocarbons having from 8 to 20 carbon atoms; (c) a plasticizer, selected from a group consisting of a liquid silicone-compatible ester, a fluid high molecular weight hydrocarbon, or a nonvolatile silicone having a viscosity between about 100 to about 10,000,000 cs; (d) a rheological modifier selected from the group consisting of trihydroxystearin; dextrin fatty acid esters; cholesterol and derivatives thereof; silicone gellants; oil soluble cellulose derivatives; oil soluble or swellable polymers or copolymers; organo-clays; polyamides; N-acyl amino acids, and esters and amides thereof; 12-hydroxystearic acid and esters and amides thereof; alkylamides of di- and tricarboxylic acids, and polyethylene; and mixtures thereof; and (e) at least one pigment or cosmetic powder; and top coat (2) comprises a primary component selected from the group consisting of nonvolatile polar esters and oils; urethanes, and mixtures thereof.

24. A method of achieving long wear of a lip product which comprises applying to the lips a base coat comprising (a) a reaction product of a silica dioxide, or a derivative thereof, with a organosiloxy resin having a viscosity of about 1000 to about 200,000 cs, and (b) a volatile carrier, allowing the base coat to dry on the lips, and applying over the base coat a separate top coat comprising a primary component that is not soluble in either water or a nonpolar hydrocarbon.

25. The method of claim 24 wherein the primary component is selected from the group consisting of nonvolatile polar esters and oils; urethanes, and mixtures thereof.

* * * * *